United States Patent [19]

Rehberg

[11] 4,441,918

[45] Apr. 10, 1984

[54] ETHYLENE INHIBITION IN PLANTS

[75] Inventor: Bobby E. Rehberg, Winter Haven, Fla.

[73] Assignee: Estech, Inc., Chicago, Ill.

[21] Appl. No.: 394,295

[22] Filed: Jul. 1, 1982

[51] Int. Cl.$^3$ ............................................. A01N 37/118
[52] U.S. Cl. ........................................ 71/113; 71/118; 71/68
[58] Field of Search ............................ 71/118, 113, 68

[56] References Cited

U.S. PATENT DOCUMENTS 2,663,629  12/1953  Semon ..................................... 71/30

OTHER PUBLICATIONS

Khaleeva et al., Chem. Abst., vol. 95 (1981), 108674y.
Auker, Chem. Abst., vol. 86 (1977) 87339q.
Amrhein et al., Chem. Abst., vol. 92 (1980), 160612d.
Amrhein et al., Chem. Abst., vol. 93 (1980), 41706y.

Primary Examiner—Catherine L. Mills
Attorney, Agent, or Firm—Jay C. Langston

[57] ABSTRACT

The use of oxamide, oxamic acid and various derivatives thereof as growth regulators is disclosed. A number of physiological effects on plants and plant tissues are set forth, and many practical uses of the invention in the agricultural field are mentioned.

7 Claims, No Drawings

ETHYLENE INHIBITION IN PLANTS

BACKGROUND OF THE INVENTION

Each plant has within its makeup a process or processes which regulate the growth of that plant. Many of these processes involve the production of ethylene and its interactions with the plant hormonal system.

Ethylene is a simple, unsaturated hydrocarbon compound and is a gas under the normal physiological conditions encountered with growing plants. Ethylene exerts a major influence on many if not all aspects of plant growth, development and senescence. Ethylene is considered a plant hormone because it is a natural product of plant metabolism, acts in trace amounts, acts in conjunction with, or is antagonistic to, other plant hormones, and is neither a substrate nor a cofactor in reactions associated with major developmental processes in plants.

Biochemical and physiological studies of ethylene biosynthesis and mode of action in plants have increased significantly in the past 25 years. Interest and activity in this field has intensified in recent years with the realization that the influence of ethylene is of considerable importance in understanding not only fruit ripening and senescence of plants but also their general hormonal activity.

Ethylene is a powerful natural regulating substance, and its effects can be observed in many areas, particularly during critical periods of the life cycle of higher plants. The influence of ethylene has been observed in practically all aspects of plant growth and development. The physiological effects of ethylene which have been reported are:
1. Stimulation of ripening of fleshy fruits.
2. Stimulation of leaf abscission.
3. "Triple response" of etiolated legume seedlings—reduced stem elongation, radial swelling of stems, and ageotropism or diageotropism of stems.
4. Inhibition of leaf and terminal bud expansion in etiolated seedlings.
5. Inhibition of root growth.
6. Increase in membrane permeability.
7. Stimulation of adventitious root formation.
8. Stimulation of flowering in pineapple.
9. Inhibition of lateral bud development.
10. Causes many types of flowers to fade and deteriorate rapidly, reducing their keeping quality.
11. Interfers with polar auxin transport.
12. Causes abscission of fruit by affecting the abscission cell layer at the fruit/stem junction.
13. Causes epinasty of leaves.

As can be seen from the above, ethylene is an important component in the matrix of hormonal regulatory factors that control plant growth, development, fruiting and senescence.

Many practical uses of ethylene have been developed in the agricultural area, such as degreening of tomatoes, oranges and other fruits to enhance marketing appeal. Ethylene-releasing materials have been developed which increase the flowering of some crops, such as pineapples. Ethylene-releasing agents have been used to make fruits, such as oranges, easier to harvest.

Applications which make use of the benefits derived from the inhibition of ethylene generation have been slower to achieve commercial success. The most significant compounds used for the inhibition of ethylene production in plant tissues are the enol ether amino acid analogs of the L-2 amino 4-alkoxytrans-3-butenoic acid molecules. These are natural products found in the fermentation broths of some microorganisms. The names of three effective amino acid analogs and their microbial origins are (1) Rhizobitoxine from *Rhizobium japonicum*, (2) Aminoethoxyvinyl glycine from *Streptomyces sp.* and (3) Methoxyvinyl glycine from *Pseudomonas aeruginosa*.

Generally speaking, aminoethyoxyvinyl glycine (AVG) is the standard ethylene inhibitor used by those studying the methionine-ethylene forming systems in higher plants.

Most of the compounds which have been identified as having the desired inhibition of ethylene are complex molecules which have been difficult to synthesize, and are therefore expensive.

It is an objective of this invention to provide inexpensive chemical compounds which will inhibit the production of ethylene in plants.

Another objective of this invention is to provide an ethylene inhibitor which acts slowly and provides ethylene-inhibiting properties over an extended period of time.

A still further objective of this invention is to provide a system which will prevent plant senescence so that carbohydrate production is prolonged, and plant yield is increased.

Other objectives include the means and systems to (a) protect flowers and plants from deterioration, especially when shipped in closed containers, (b) increase the yields of plants by preventing flower abortion, fruit drop and abscission of desirable vegetative parts, and (c) improve the quality of turf by maintaining chlorophyll levels, increasing clipping yields, preventing leaf senescence and increasing disease resistance.

Additional objectives and advantages of the invention will appear from the description of the invention that follows.

SUMMARY OF THE INVENTION

This invention relates to plant growth-regulating compounds which inhibit ethylene generation by using oxamide, oxamic acid and alkai metal salts or lower alkyl esters of the acid. Oxamide has long been recognized as an effective slow-release nitrogen source for fertilization of turf grasses and crops. However, the ability of oxamide, oxamic acid and related salts and esters to inhibit ethylene generation in plants had not been discovered prior to this invention. Oxamide and its hydrolysis product, oxamic acid, are shown to be effective inhibitors of the plant growth regulator, ethylene.

DETAILED DESCRIPTION OF THE INVENTION

This invention concerns a method of regulating plant growth through inhibiting ethylene production, which method comprises treating the plant with an effective but non-injurious amount of a member selected from the group consisting of oxamide and oxamic acid and its alkali metal salts and esters of one to eight hydrocarbons or mixtures of any of the above.

The growth regulators of this invention can be used to protect flowers and plants from deterioration, especially when shipped in closed containers. In some instances, merely the stem of the flower is placed in an aqueous suspension of oxamide. In other cases, the entire plant may be sprayed with the solution.

Using the growth regulators of this invention, it is possible to achieve retardation of ripening of the harvest product, before or after harvesting. This is of particular advantage since it is thereby possible to achieve optimum adaptation of produce ripeness to market requirements.

It is not known with certainty whether the oxamide or oxamic acid is acting as the ethylene inhibitor. From the examples, it appears that both compounds possess this property. This is not important, however, since some oxamide immediately hydrolyzes to oxamic acid in the presence of water and it is this solution that is effective in inhibiting ethylene production.

In general, the plant growth regulators of this invention are effective down to about $10^{-6}$ M. A preferred range is $10^{-1}$ M to $10^{-6}$ M.

Oxamide is a white, crystalline substance with a nitrogen content of 31.8%. It is sparingly soluble in water to the extent of about 0.4 g per liter at 20° C. It is not hygroscopic, has a melting point above 200° C. and decomposes at 290° C. Oxamide is relatively non-toxic, stable and can be stored indefinitely.

Oxamide is a relatively old compound, and several methods are described in the literature concerning its preparation. Accordingly, only a brief description of oxamide manufacture need be set forth. One of the methods for oxamide production is the Hoechst process. The starting material is hydrogen cyanide, which can be directly synthesized using known procedures or it can be obtained as a by-product of acrylonitrile manufacture. The oxamide-forming reaction is a catalytic oxidation of the hydrogen cyanide in a liquid phase. Oxygen or air is used as the oxidizing agent. The reaction gives an almost quantitative yield, and the resulting oxamide is of high enough purity to be used without further purification. Other various routes for the preparation of oxamide are known. However, the preparation of oxamide is not part of this invention and, hence, no detailed description of the various processes need be set forth.

In one aspect of this invention, premature shedding of fruit can be prevented by the use of oxamide or oxamic acid. These materials can be used to reduce the losses incurred in such crops as apples and citrus where premature fruit drops reduce the harvest.

In addition to its activity as an ethylene inhibitor, oxamide and oxamic acid have the added benefit of a very low water solubility. This low solubility slows the physiological availability of the compound to the plant and provides ethylene-inhibiting activity over an extended period of time.

One development in the past 20 years, which is considered important in recognition and expansion of research on ethylene in plant physiology, is the use of gas chromatography. Gas chromatography allows a rapid, sensitive and simple assay of the ethylene evolved by plant tissues. As a consequence, ethylene is currently the easiest plant hormone to assay, because it is a gas which evolves from the plant tissues, requires no extraction or purification prior to analysis, and can be accurately measured by a gas chromatograph.

The following examples are set forth at this time as illustrative embodiments of this invention and are not to be taken in any manner as limiting the scope of the invention which is defined by the appended claims.

Ethylene inhibition tests were conducted on orange peels, whole oranges, and orchids. Results of these tests were as follows:

EXAMPLE I

Explants of orange peel 10 mm in diameter were cut from the peel with a cork borer and placed in sealed vials after being exposed to various experimental ethylene-inhibiting materials. The concentration of ethylene was determined at 48 and 72 hours by gas chromatography. Vials were flushed after the initial sampling. (Methods of Evensen, Biggs, et al., J. American Society Horticultural Science 106 (1) 57–60, 1981.) Three explant discs were used in each vial, with 4 replications.

| ETHYLENE PRODUCTION nl/hr/3 discs | | | | |
|---|---|---|---|---|
| | | 48 Hours | | 72 Hours |
| Control (H₂O) | | | | |
| 1 | | 5.2 | | 4.6 |
| 2 | | 4.75 | | 3.7 |
| 3 | | 5.8 | | 4.3 |
| 4 | | 5.05 | | 4.9 |
| | Mean | 5.15 | | 4.38 |
| Amino vinyl glycine (AVG) at $10^{-3}$M | | | | |
| 1 | Less than | 0.4 | Less than | 1.2 |
| 2 | " | .1 | " | .1 |
| 3 | " | .1 | " | .1 |
| 4 | " | .1 | " | .1 |
| | Mean | .1 | Approx. | .3 |
| Ethrel (Control) at $10^{-3}$M | | | | |
| 1 | | 22.5 | | 13.0 |
| 2 | | 18.7 | | 17.8 |
| 3 | | 26.0 | | 12.3 |
| 4 | | 19.1 | | 7.9 |
| | Mean | 21.58 | | 9.5 |
| Oxamide at $10^{-6}$M | | | | |
| 1 | Less than | .1 | Less than | .1 |
| 2 | " | .1 | " | .1 |
| 3 | " | .1 | " | .1 |
| 4 | " | 1.2 | " | 3.1 |
| | Approx. | 0.3 | Approx. | 0.8 |
| Oxamic Acid at $10^{-6}$M | | | | |
| 1 | Less than | .1 | Less than | .1 |
| 2 | " | .1 | " | .1 |
| 3 | " | .1 | " | .1 |
| 4 | " | .1 | " | .1 |
| | Mean | 0.1 | | 0.1 |

CONCLUSION: Oxamide and its hydrolysis product, oxamic acid, at $10^{-6}$ M are as active as aminovinylglycine at $10^{-3}$ M in the inhibition of ethylene in orange peel discs.

AVG is one of the most potent ethylene inhibitors ever discovered; however, it was never commercialized due to high production costs.

EXAMPLE II

Whole citrus fruits (oranges) were immersed in solutions of various ethylene-inhibiting materials, taking care not to wet the stem area.

The internal ethylene concentration was sampled with a hypodermic needle and analyzed by gas chromatography. Condition of the abscission zone of the stem/fruit was also noted.

| PPM ETHYLENE PRODUCTION WHOLE CITRUS FRUIT 96 HOURS | |
|---|---|
| | PPM Internal Ethylene |
| Control | |
| 1 | 1.1 |

-continued

PPM ETHYLENE PRODUCTION WHOLE CITRUS FRUIT 96 HOURS

| | | PPM Internal Ethylene |
|---|---|---|
| 2 | | 0.9 |
| 3 | | 0.75 |
| 4 | | 2.4 |
| | Mean | 1.3 |
| Aminovinylglycine $10^{-3}$M | | |
| 1 | Less than | 0.05 |
| 2 | " | 0.05 |
| 3 | " | 0.05 |
| 4 | " | 0.05 |
| | | 0.05 |
| Ethrel | | |
| 1 | | 11.1 |
| 2 | | 9.6 |
| 3 | | 13.8 |
| 4 | | 5.2 |
| | Mean | 9.73 |
| Oxamide $10^{-6}$M | | |
| 1 | Less than | 0.05 |
| 2 | " | 0.05 |
| 3 | " | 0.05 |
| 4 | " | 1.02 |
| | Approx. | 0.25 |
| Oxamic Acid $10^{-6}$M | | |
| 1 | Less than | 0.05 |
| 2 | " | 0.05 |
| 3 | " | 0.05 |
| 4 | " | 0.05 |
| | | 0.05 |

CONCLUSIONS:

1. Oxamide and oxamic acid were very effective in virtually stopping ethylene production in whole fruit at very low concentrations ($10^{-6}$ M).

2. Oxamic acid may be more active than oxamide itself; however, the one high value may be experimental error.

3. Oxamide and oxamic acid were absorbed very rapidly by the fruit. Ethylene production in fruit is the primary reason for the fruit drop in apples, peaches, oranges, and others.

A buildup of internal ethylene causes the abscission layer at the stem/fruit junction to weaken, allowing the fruit to drop. Examination of stems at the termination of the experiment indicated the following:

(1) Ethrel-treated fruits dropped their stems within 12 hours after treatment.

(2) Most of the control orange stems had dropped off by 48 hours or were very easy to remove at 96 hours.

(3) The oranges treated with AVG, oxamide, or oxamic acid were all attached and very difficult to remove, indicating a blockage of the ethylene production at 96 hours.

EXAMPLE III

Orchid Flower Tests-Blossoms from several varieties of orchids fade prematurely when their pollinia are removed (Akamine, E. A. Science 140:1217-18, 1963), and also if gassed by ethylene (Arditti, et al., Amer. J. Bot. 60 (9):883-88, 1973) or pollinated or treated with an auxin (Burg, S. P. and Dijkman, M. J., Plant Phys:01 42:16848-50, 1967). Pollination, emasculation (pollinia removal) and auxin treatments can all cause ethylene evolution. This is especially a problem when shipping flowers in closed containers where damage to many flowers can occur from dislodgement of pollinia from a single flower.

EXPERIMENTAL PROCEDURE 1: Cattleya orchid flowers were dipped for 30 minutes in water, $10^{-4}$ M oxamide, and $10^{-4}$ M oxamic acid, emasculated, and placed in a one-gallon collection jar equipped with a rubber septum for gas sampling. Ethylene concentration was determined after 24 hours by gas chromatography. Values are means of two treatments.

| PPB ETHYLENE EVOLUTION OF EMASCULATED CATTLEYA ORCHID FLOWERS AFTER 24 HOURS | |
|---|---|
| Treatment | PPB Ethylene |
| 1. Water Dip | 700 |
| 2. Oxamide $10^{-4}$M | 217 |
| 3. Oxamic Acid $10^{-4}$M | 30 |

EXPERIMENTAL PROCEDURE 2: Stems of Phalonopsis orchid flowers were fitted through a rubber septum into various solutions for stem uptake. All flowers except a control were emasculated and placed in a one-pint sealed container equipped with a septum for gas sampling. Containers were sampled 21 hours later. Values are means of two treatments.

| PPB ETHYLENE EVOLUTION OF PHALONOPSIS ORCHID FLOWERS TREATED BY STEM UPTAKE | |
|---|---|
| Treatment | PBB Ethylene |
| 1. Non-Emasculated | 10 |
| 2. Emasculated | 83 |
| 3. Oxamide $10^{-4}$M | 283 |
| 4. Oxamic acid $10^{-4}$M | 10 |
| 5. Zeatin Riboside 2 ppm | 83 |

At the end of 100 hours, containers were opened and flowers examined. Non-emasculated controls and $10^{-4}$ M oxamic acid-treated, emasculated flowers were in good condition and salable.

Flowers treated by $10^{-4}$ M oxamide were apparently damaged by free ammonia in the closed containers. Emasculated controls were collapsed, bleached and unusable.

As can be seen from the above description of the invention, aqueous solutions of oxamide and its hydrolysis product, oxamic acid, are very effective inhibitors of ethylene in plants. Specific areas include the use of oxamide and oxamic acid and its $C_1$-$C_8$ esters or alkali metal salts as endogenous ethylene inhibitors in plants. These compounds can be used to improve the quality and disease resistance of turf, ornamental plants, crops or other desirable plant parts. The compounds utilized in this invention can also be used to reduce the tendency for abscission in fruit, to protect flowers and vegetables during shipment, and to reduce plant senescence, thus extending the useful life and productivity of plants. Further, these compounds can be used to enhance the capability of plants to resist the invasion of disease organisms. Accordingly, one skilled in the art will readily understand the various uses that can be made of this invention and the scope of this invention is not to be limited to the specific examples set forth above as they are merely illustrative of the broad area of this invention.

Obviously, many modifications and variations of the invention as hereinbefore set forth may be made without departing from the spirit and scope thereof, and only such limitations should be imposed as are indicated in the appended claims.

I claim:

1. A method of regulating plant growth by effecting ethylene inhibition which comprises treating the plant with an effective but non-injurious amount of a member selected from the group consisting of oxamide and oxamic acid and its lower alkyl esters and alkali metal salts or mixtures thereof, said amount being in the order of about $10^{-1}$ M to $10^{-6}$ M.

2. The method of claim 1 wherein the member of the group is oxamide.

3. The method of claim 1 wherein the member of the group is oxamic acid.

4. The method of claim 1 wherein the member of the group is used in an amount of about $10^{-6}$ M.

5. The method of claim 1 wherein the ethylene is inhibited so as to reduce fruit abscission.

6. The method of claim 1 wherein the plant is flowers and ethylene is inhibited so as to protect the flowers during shipment or to maintain their useful life after cutting.

7. The method of claim 6 wherein the flowers are orchids and the blossoms are treated.

* * * * *